(12) United States Patent
Raikhel et al.

(10) Patent No.: US 6,747,190 B1
(45) Date of Patent: Jun. 8, 2004

(54) XYLOGLUCAN FUCOSYLTRANSFERASE PLANTS TRANSFORMED WITH A DNA ENCODING ARABIDOPSIS

(75) Inventors: Natasha V. Raikhel, Okemos, MI (US); Kenneth G. Keegstra, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/037,311

(22) Filed: Nov. 9, 2001

Related U.S. Application Data

(63) Continuation of application No. 09/490,521, filed on Jan. 25, 2000, now abandoned.
(60) Provisional application No. 60/117,555, filed on Jan. 28, 1999.

(51) Int. Cl.[7] ............................. A01H 5/00; C12N 15/82
(52) U.S. Cl. ....................................... 800/298; 800/284
(58) Field of Search ................................ 800/298, 284; 336/23.2, 23.6

(56) References Cited

PUBLICATIONS

Rounsley et al, 1998, EMBL Accession No. T02704.*
Newman et al, 1994, GenBank Accession No. R90192.*
Faik et al, 2000, J. Biol. Chem. 275:15082–15089).*
Leiter et al, 1999, J. Biol. Chem. 274:21830–21839.*
Hill et al, 1998, Biochem. Biophys. Res. Comm. 244:573–577.*
Staudacher et al, 1999, Biochim. Biophys. Acta 1473:216–236.*

* cited by examiner

Primary Examiner—Anne R. Kubelik
(74) Attorney, Agent, or Firm—Ian C. McLeod

(57) ABSTRACT

Plant cell walls play a crucial role in development, signal transduction, and disease resistance. They are made of cellulose and matrix polysaccharides such as hemicelluloses and pectins. Xyloglucan, the principal hemicellulose of dicotyledonous plants, has a terminal fucosyl residue that may affect the extensibility of the cell wall and thus influence plant growth and morphology. The fucosyltransferase (FTase) that adds this residue was purified from pea epicotyls. Peptide sequence information derived from the 62 kDa purified pea FTase made it possible to clone a homologous gene from Arabidopsis. The instant invention involves methods of expressing the Arabidopsis FTase gene in plants and plants thereby obtained.

2 Claims, 1 Drawing Sheet

XYLOGLUCAN FUCOSYLTRANSFERASE PLANTS TRANSFORMED WITH A DNA ENCODING ARABIDOPSIS

CROSS-REFERENCE TO RELATED APPLICATION

This application is a continuation of U.S. application Ser. No. 09/490,521, filed Jan. 25, 2000 now abandoned which claims the benefit of provisional application Serial No. 60/117,555, filed Jan. 28, 1999.

FIELD OF THE INVENTION

This invention is in the field of molecular biology. In particular, this invention relates to the isolation, purification, cloning and expression of plant xyloglucan fucosyltransferases.

BACKGROUND OF THE INVENTION

In most multicellular organisms, cells are embedded in an intricate extracellular matrix that keeps them together and influences the shape, development, and polarity of the cells they contact. Animal cells have such an extracellular matrix at their surface, but plants possess a distinct wall that encloses every cell. Many important differences between plants and animals with respect to nutrition, digestion, growth, reproduction, and defense mechanisms can be traced to the plant cell wall. Cell walls are mediators of growth, which in plants is determined largely by the wall extensibility provided that sufficient turgor pressure is present. Morphogenesis is also effected by the cell wall at the tissue and cellular levels. The biosynthesis of plant cell walls must be very tightly regulated. Although an individual plant cell may expand its volume by as much as 18,840 times, its cell wall must maintain a regular thickness and uniform structure to prevent hemorrhaging of the cell contents due to the high internal turgor pressure. However, despite extensive descriptions of the chemical and physical structure of the plant cell wall, very little is known about its biosynthesis. Only one cell wall-synthesizing glycosyltransferase, cellulose synthase, has been cloned and described in any detail Plant cell walls are mainly composed of cellulose microfibrils and matrix polysaccharides. Hemicellulose is a type of matrix polysaccharide that binds tightly but noncovalently to cellulose microfibrils, helping to crosslink them into a complex network. Xyloglucan is a fundamentally important hemicellulose in dicot and nongraminaceous monocot plants. It comprises approximately 25% of the total cell wall and forms a load-bearing network by associating with the faces of surrounding cellulose microfibrils via hydrogen bonds. Xyloglucan contains a beta-1,4-glucan backbone decorated with side chains of xylose alone, xylose and galactose, and xylose, galactose and fucose. The presence or absence of the fucose residue is thought to determine whether the xyloglucan conformation is planar and thus better able to bind to cellulose, a critical step in cell wall formation. In addition, oligosaccharides consisting of a monomer of xyloglucan have been shown to prevent auxin-promoted elongation of pea stems when the oligosaccharides contain fucose, but not if they lack fucose suggesting that xyloglucan fragments act as signalling molecules in vivo. Xyloglucan fucosylation is thus a critical step in plant development.

There is thus a need to identify the genes and gene products involved in plant xyloglucan fucosylation. In particular, there is a need to isolate, purify and clone xyloglucan fucosyltransferase genes and gene products so that xyloglucan fucosylation may be controlled and regulated in plants and other organisms.

SUMMARY OF THE INVENTION

In order to meet these needs, the present invention is directed to purified, isolated, sequenced and cloned plant xyloglucan fucosyltransferase. In addition, the present invention is directed to the purification, isolation, sequencing and cloning of plant xyloglucan fucosyltransferase. The present invention is further directed to transgenic organisms expressing plant xyloglucan fucosyltransferase. The present invention is further directed to transgenic plants expressing regulated levels of xyloglucan fucosyltransferases.

In general, the invention features substantially pure fucosyltransferase DNA or protein obtained from a plant. In a related aspect, the invention features a fragment or analog polypeptide including an amino acid sequence substantially identical to the sequences shown in SEQ ID NOs: 1, 5 and 7.

In another related aspect the invention features substantially pure DNA having a sequence substantially identical to the nucleotide sequence shown in SEQ ID NOs: 2, 3, 4, 6, 8, 9, 10, 11, 12, 13, 14, and 15. In preferred embodiments, such DNA is cDNA or is genomic DNA. In related aspects, the invention also features a vector and a cell (e.g., a plant) which includes such substantially pure DNA. In various preferred embodiments, the vector-containing cell is a prokaryotic cell, for example, E. coli or Agrobacterium or, more preferably, a plant cell.

In yet another related aspect, the invention features a method of fucosylating a polypeptide in vivo involving: (a) providing a cell containing the fucosyltransferase DNA of the invention positioned for expression in the cell; and (b) culturing the transformed cell under conditions for expressing the DNA, resulting in the fucosylation of the protein. In preferred embodiments, fucosylation occurs in a plant cell.

In another aspect, the invention features a recombinant polypeptide fucosylated using a cell expressing DNA which is substantially identical to the nucleotide sequence shown in SEQ ID NOs: 2, 3, 4, 6, 8, 9, 10, 11, 12, 13, 14, and 15. In still other preferred embodiments, the polypeptide is further fucosylated using one or more fucosyltransferases.

The present invention further includes multiple types of DNA constructs including (1) "sense" constructs encoding proteins, which can increase the expression of fucosyltransferases in plant species and (2) "antisense" constructs containing DNA, which can be used to produce antisense RNA in to reduce expression of fucosyltransferases in plants. Optimal amounts of antisense RNA in transgenic plants will selectively inhibit the expression of genes in these plants which are involved in the fucosylation of xyloglucans.

Some of these constructs will direct constitutive production of transcripts. Other constructs will direct expression in specific organs and/or specific tissue layers of the transgenic plant. These organs will include leaves, petioles, stems, flower organs, seeds, fruits or photosynthetically active parts of the plant. Tissue layers will include but may not be restricted to the epidermis and adjacent cell layers.

The present invention also provides recombinant cells and plants containing these constructs.

In one embodiment, the first category of DNA constructs include: a promoter selected from but not limited to constitutive, tissue-specific, cell-type specific, seed-specific, flower-specific, fruit-specific, epidermis-specific promoters, a promoter specific to cell layers adjacent to the epidermis or a promoter specific to photosynthetically active plant tissues, which functions in plant cells to cause the production of an RNA sequence. In this embodiment, the DNA coding region sequences that encode proteins which can be used to increase the activity of plant fucosyltransferases in transgenic plants. The DNA coding region will further include a region 3' to the coding regions the 3' non-translated region which functions in plant cells to cause the addition of polyadenylate nucleotides to the 3' end of the RNA sequence promoter.

In another embodiment, a second category of DNA construct will include a constitutive promoter, seed-specific, flower-specific, fruit-specific, epidermis-specific promoter, a promoter specific to cell layers adjacent to the epidermis or a promoter specific to photosynthetically active plant tissues, which functions in plant cells to cause the production of an RNA sequence. The DNA construct will also include DNA sequences which can produce antisense RNA molecules. These RNA molecules can selectively inhibit the accumulation of transcripts encoding proteins which encode plant fucosyltransferases.

In accordance with another aspect of the present invention, there is provided a method of producing genetically transformed plants which express a gene or genes involved in fucosyltransferase activity. In this method, a recombinant, double-stranded DNA molecule is incorporated into the genome of a plant cell. In this embodiment, the DNA sequence will include a promoter which functions in plant cells to cause the production of an RNA sequence in flowers, seeds, fruit or other plant tissues. In addition, the sequence will include a DNA coding sequence encoding proteins involved in fucosyltransferase activity in plants. Alternatively, the sequence will be a template to the synthesis of antisense RNA inhibiting the development of these structures. The DNA sequence will also include a 3' non-translated region which functions in plant cells to cause the addition of polyadenylate nucleotides to the 3' end of the RNA sequences. The method also includes obtaining transformed plant cells and regenerating from the transformed plant cells genetically transformed plants. The transformed plant cells may be used to overproduce in cell culture the fucosylated xyloglucans.

The present invention is also directed to transgenic cells such as yeast, fungi, mammalian, and the like cells expressing the DNA sequences of this invention. The present invention is also directed to purified fucosylated xyloglucans isolated from the transgenic cells of the invention.

DEFINITIONS

Figure 1:
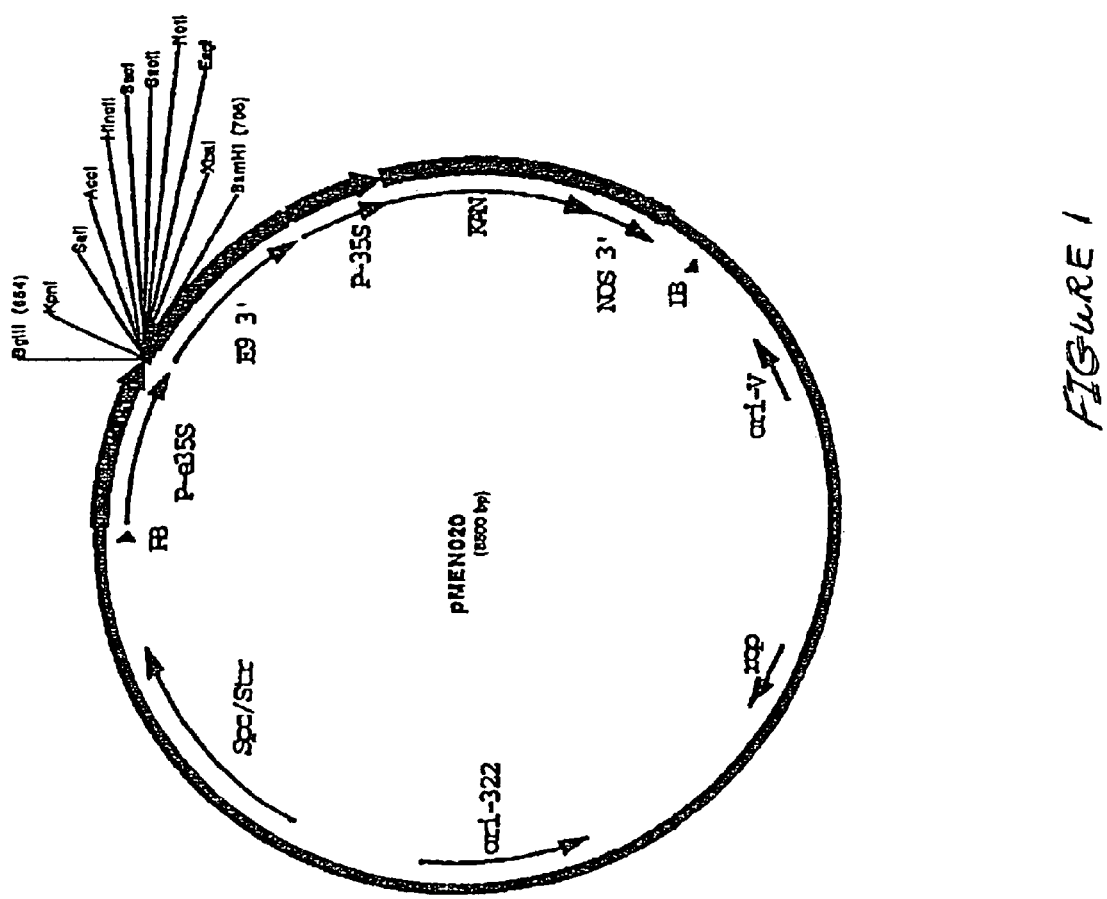
FIG. 1 shows a diagram of plasmid pMEN020.

To ensure a complete understanding of the invention, the following definitions are provided:

Xyloglucan: Xyloglucan is a hemicellulose carbohydrate present in dicot and nongraminaceous monocot plants comprising approximately 25% of the total cell wall and forming a load-bearing network by associating with the faces of surrounding cellulose microfibrils via hydrogen bonds. Xyloglucan contains a beta-1,4-glucan backbone decorated with side chains of xylose alone, xylose and galactose, and xylose, galactose and fucose.

Xyloglucan fucosyltransferase: Xyloglucan fucosyltransferase (XG FTase) is an enzyme that fucosylates xyloglucan by adding a fucose residue to xyloglucan.

Transgenic Plants: Transgenic plants are plants which contain DNA sequences which were introduced by transformation.

Promoter: A promoter is the minimal DNA sequence sufficient to direct transcription. Promoters can render transcription controllable for cell-type specific, tissue-specific, or inducible expression. Promoter elements may be located in the 5' or 3' regions of the native gene.

Poly-A Addition Site: A poly-A addition site is a nucleotide sequence which causes certain enzymes to cleave mRNA at a specific site and to add a sequence of adenylic acid residues to the 3'-end of the mRNA.

Polypeptide: Polypeptide means any chain of amino acids, regardless of length or post-translational modification (e.g., glycosylation or phosphorylation).

Substantially Identical: For a polypeptide, substantially identical means a polypeptide exhibiting at least 50%, preferably 70%, more preferably 90%, and most preferably 95% identity to a reference polypeptide. For a nucleic acid substantially identical means a nucleic acid sequence exhibiting at least 85%, preferably 90%, more preferably 95%, and most preferably 97% identity to a reference nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 30 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Substantially Pur Polypeptid: Substantially pure polypeptide means a fucosyltransferase polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight fucosyltransferase polypeptide. A substantially pure fucosyltransferase polypeptide may be obtained, for example, by extraction from a natural source (e.g., a plant) by expression of a recombinant nucleic acid encoding a fucosyltransferase polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include, without limitation, those derived from eukaryotic organisms but synthesized in *E. coli* or other prokaryotes, or those derived from a eukaryotic cell which does not normally synthesize such a protein, or those derived from a eukaryotic cell engineered to overexpress such a protein.

Substantially Pure DNA: Substantially pure DNA means DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

Transformed Cell: Transformed cell means a cell into which (or into an ancestor of which) has been introduced, by means of recombinant DNA techniques, a DNA molecule encoding (as used herein) a fucosyltransferase polypeptide.

Positioned for Expression: Positioned for expression means that the DNA molecule is positioned adjacent to a DNA sequence which directs transcription and translation of the sequence (i.e., facilitates the production of, e.g., a recombinant fucosyltransferase polypeptide or RNA molecule).

Operably Linked: Operably linked mean that a gene and a regulatory sequence(s) are connected in such a way as to permit gene expression when the appropriate molecules (e.g., transcriptional activator proteins) are bound to the regulatory sequence(s).

Purified Antibody: Purified antibody means an antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., a plant fucosyltransferase specific antibody. A purified fucosyltransferase antibody may be obtained, for example, by affinity chromatography using recombinantly-produced fucosyltransferase protein or conserved motif peptides and standard techniques.

Specifically Binds: Specifically binds means an antibody which recognizes and binds fucosyltransferase protein but which does not substantially recognize and bind other molecules in a biological sample.

DETAILED DESCRIPTION OF THE INVENTION

Taking into account these definitions, the present invention is directed to isolated, purified and cloned plant xyloglucan fucosyltransferases.

Plant Fucosyltransferase Purification

A biochemical approach was utilized to purify sufficient quantities of xyloglucan fucosyltransferases from pea epicotyls. Pea microsomes were prepared as follows: 2 cm segments, excised just below the apical hook, of etiolated Pisum sativum, cv Alaska were collected and homogenized in 1.5 volumes buffer (50 mM Hepes pH 7.5, 1 mM EDTA pH 8.0, 0.4 M sucrose, 1 mM DTT, 0.1 mM PMSF, 1:g/mL each aprotinin, leupeptin, and pepstatin.) The homogenate was filtered, centrifuged at 2,000×g for 15 minutes, and the supernatant was centrifuged at 100,000×g for 1 hour. The resulting pellets were washed and homogenized in the presence of 0.1 M $Na_2CO_3$ to strip away peripheral membrane proteins (Y. FuJiki, A. L. Hubbard, S. Fowler, P. B. Lazarow, J. Cell Biol. 93, 97 (1982).) The suspension was t centrifuged at 100,000×g for 1 hour and the resulting pellets were washed and resuspended in buffer (50 MM Pipes-KOH pH 6.2, 20% glycerol, 1 mM EDTA, 1 mM DTT, 0.1 M PMSF, 1:g/mL each aprotinin, leupeptin, and pepstatin.) The suspension was homogenized, mixed with TritonX-100 to a final volume of 0.8%, and stirred for 1–2 h to solubilize membrane proteins. The suspension was centrifuged a final time at 100,000×g for 1 h and the supernatant was collected and saved.

Arabidopsis cell suspension culture was also used as a tissue source. When Arabidopsis cell suspension culture was used, the purification procedure was the same except the cells were lysed an a French pressure cell at 4000 p.s.i.

Pea carbonate-washed supernatents were pooled and separated on a GDP-HA agarose affinity chromatography column and GDP-binding proteins were eluted using excess free GDP. Protein levels were monitored by A280. The protein samples were desalted on a Sephadex G-25 column, concentrated, and further separated on a Phenomenex SEC 4000 size exclusion column. Some samples were further purified using a Poros QE or Resource Q anion exchange column and subsequently column and separated by SDS-PAGE electrophoresis.

Fucosyltransferase Assay

A specific assay for fucosyltransferase was developed using tamarind or nasturtium storage xyloglucan, which naturally lack fucosyl residues, as an acceptor and radiolabeled GDP-fucose as a donor [V. Farkas, G. Maclachlan, *Arch. Biochem. Biophys.* 264, 48 (1988). A. Camirand, D. Brummell, G. Maclachlan, *Plant Physiol.* 84, 753 (1987)].

Carbohydrate Analysis

To confirm that the purified pea protein synthesizes an alpha-1,2 fucose:galactose linkage, carbohydrate analysis was performed on the product resulting from in vitro fucosylation of tamarind xyloglucan by purified FTase. Carbohydrate linkage analysis of tamarind xyloglucan before (tamarind xg) and after (fucosylated xg) incubation with purified pea FTase. Samples were incubated at room temperature for 20 minutes (for immunoprecipitation samples) or 30 minutes (for protein purification samples) with 25 mM Pipes-KOH pH 6.2, 0.5 mg/mL tamarind xyloglucan, 0.05% $^3$H GDP-fucose (3.7 mBq/mL, 300 GBq/mM, NEN, Boston, Mass.). Most assays also contained 50:M non-radiolabeled GDP-fucose to provide a quantitative measurement of enzyme activity. Assays of immunoprecipitation samples also contained 5 mM $MgCl_2$. Reactions were precipitated using 70% ethanol and $^3$H incorporation was measured by scintillation counting. The amount of fucose incorporated into the product was used to calculate activity in nanokats (nKat—nMoles substrate incorporated into product per second.) The results are shown in Table 1.

TABLE I

| Sugar Residue | % tamarind xg | % Fucosylated xg |
|---|---|---|
| 4-glucose | 16.4 | 17.5 |
| 4,6-glucose | 37.0 | 31.5 |
| t-xylose | 19.0 | 13.5 |
| 2-xylose | 15.0 | 14.3 |
| t-galactose | 12.6 | 5.5 |
| 2-galactose | — | 9.0 |
| t-fucose | — | 8.7 |

Tamarind seed xyloglucan was fucosylated by 33 pKat size exclusion column-purified pea FTase (1 mg/mL tamarind XG, 1.5 mM GDP-fucose, 50 mM Pipes-KOH pH 6.2.)

XG product was precipitated with ethanol, resuspended in water, reprecipitated, and sent to the Complex Carbohydrate Research Center (Athens, Ga.) for linkage analysis. An equal amount of tamarind xyloglucan was also submitted for linkage analysis. Linkage analysis indicated that incubation of XG with purified FTase resulted in a decrease in the mole percentage of terminal galactose and the appearance of 2-galactose and terminal facose, thus verifying the activity of the purified enzyme.

Peptide Sequencing

It was possible to purify XG FTase 1400-fold by the end of the size exclusion chromatography step resulting in a total of 0.05 mg protein containing 70 nKat XG FTase activity. After biochemical purification and subsequent assay analysis, two polypeptides of approximately 65 kDa and 60 kDa in size were observed to co-purify repeatedly with XG FTase activity.

Limited peptide sequence was obtained from both proteins. Proteins in size exclusion column eluate fractions containing peak amounts of FTase activity were concentrated using a Millipore 4 mL 10 kDa concentrator and separated by electrophoresis. After brief staining with Coomassie and destaining the separated proteins were excised, rinsed in 50S acetonitrile, stored at −80° C. and sent to Harvard Microchemistry (Cambridge, Mass.) for tryptic peptide sequencing. Six peptide sequences were obtained: VFGFLGR (SEQ ID NO: 16), YLLHPTNNVWGLVVR (SEQ ID NO: 17), AVLITSLSSGYFEK (SEQ ID NO: 18), YYDAYLAK (SEQ ID NO: 19), LLGGLLADGFDEK (SEQ ID NO: 20), and ESILPDVNR (SEQ ID NO: 21).

Arabidopsis EST Identification

Using these peptides as a query in the Blastp program identified an Arabidopsis EST, 191A6T7, which contained four out of six peptides in a deduced translation of a potential ORF. The 65 kDa peptide was identified as a homolog of BiP, the usually ER-localized molecular chaperone. It is possible that this chaperone co-purified with FTase activity as an artifact and prevented the denaturation of the FTase during purification, though this has not been confirmed.

Peptides from the lower molecular weight protein were not significantly similar to proteins of known function in databases, but did allow the identification of an Arabidopsis EST which, when translated contains four out of six peptides with amino acid identity ranging from 63%–85%.

The EST(number 191A6t7) was analyzed to determine if it was a full length clone. Northern blot analysis using the ~900 bp-long 191A6T7 as a probe detected an approximately 2 kb transcript, indicating that the EST did not contain the full-length cDNA (RMP, data not shown.).

191A6T7 was used as a probe to screen the CD4–15 portion of a size-fractionated Arabidopsis cDNA library at high stringency (J—J—Kieber, M. Rothenberg, G. Roman, K. A. Feldmann, J. R. Ecker, Cell 72, 427 (1993). Two cDNA clones were isolated, the longest containing a 1768 bp insert. Both lacked 13 nucleotides of the 3' UTR and the poly-A tail found in 191A6T7. There is an AATAAA consensus polyadenylation signal eight nucleotides from the 3' end of the library-derived clones. The sequence contains a 1698 nucleotide ORF that encodes a 63.7 kDa protein a 1698 nt open reading frame and correspond to a region of the fully sequenced Arabidopsis bacterial artificial chromosome (BAC) T18E14.

The cDNA and corresponding genomic clone have been designated AtFT1. Interestingly, analysis of the BAC indicates that there may be a second FTase approximately 600 bp downstream from AtFT1 which is ~60% identical to AtFT1. Whether this second FTase is expressed, as well as splicing patterns and localization of the encoded protein, are matters of current investigation. It does raise the possibility that a multi-gene family of FTases may exist in Arabidopsis. We will determine whether members of such a family might be differentially regulated by such factors as environmental stress, tissue localization, or developmental stage. Alternatively, there may well be FTases which have different acceptors, such as carbohydrate protein modifications.

Antibody Preparation

In order to confirm the identity of AtFT1 as encoding a xyloglucan-specific fucosyltransferase, we prepared polyclonal antibodies directed against AtFT1 and used them to immunoprecipitate proteins from carbonate-washed, solubilized Arabidopsis proteins.

The portion of AtFT1 encoding aa 73 to 566 was PCR-amplified using appropriate primers and cloned into the pET28a expression vector (Novagen, Madison Wis.) The resulting insoluble fusion protein was purified by washing four times with 1% Triton X-100, 50 mM Hepes-KOH pH 7.6, 10 MM $MgCl_2$ and one time with 25 mM Hepes-KOH pH 7.0, 8 M urea. The pellet was resuspended in 6 M guanidine-HCl and protein was precipitated from the supernatant with 10% TCA. The protein was emulsified with Titermax adjuvant (CytRx Corporation, Norcross, Ga.) and injected into a rabbit. For western blotting, 40:1 of carbonate-washed solubilized protein from pea and Arabidopsis and 50 ng of purified antigen were separated by SDS-PAGE and electroblotted. Anti-AtFT1 Abs (1:5000) were used for western blotting. Goat-antirabbit antibodies conjugated to horseradish peroxidase was used as a secondary antibody. Signals were detected by the enhanced chemiluminescence method (Pierce, Rockford, Ill.). Membranes were then stained with Coomassie blue to detect protein.

Immunoprecipitations

For immunoprecipitations, solid NaCl was added to carbonate-washed solubilized Arabidopsis protein to a final concentration of 200 mM. The Arabidopsis protein was precleared by incubation with 1/10 volume of 50% slurry of protein A sepharose beads (Pharmacia) in buffer A (25 mM Pipes-KOH pH 7.5, 50 MM NaCl, 2 mM EDTA pH 8.0.) The resulting supernatants were incubated with 50:1 of immune or preimmune anti-AtFT1 serum for 1 h. ⅕ volume of protein A sepharose slurry was added to precipitate the antigen-antibody complexes and the samples were incubated for an additional 3 hours with rocking at 4 degrees C. Samples were then centrifuged, washed five times in buffer A containing 1% Triton X-100 and two times in buffer A without detergent. The pellets were resuspended in buffer A to a final volume of 120:1 and assayed for AtFTase activity as described above.

The immunoprecipitated proteins were then assayed for XG FTase activity. More FTase activity was correlated with pellets derived from immunoprecipitation reactions using immune antiserum rather than preimmune serum, thereby indicating that the Arabidopsis clone encodes a xyloglucan-specific FTase.

Expression in COS Cells

Cos-7 cells were grown on 100 mm plates in DMEM-10% Fetal Bovine Serum. Cells were transfected with different plasmids using Lipofectamine™ reagent (Life Technologies) following the manufacturer's instructions using 9:g of DNA and 72:g of Lipofectamine. Cells were incubated for 24 hours in the medium containing DNA-Lipofectamine without Fetal Bovine Serum. The medium was changed to DMEM-10% Fetal Bovine Serum and incubated for another 48 hours. The cells were scraped off the dish in 0.25 M sucrose, 10 mM Tris-HCl pH 7.5 and 0.4% CHAPS. XG-FTase activity was measured using 50:g of protein in the absence (−XG) or presence (+XG) of 100:g tamarind xyloglucan. The incubation was carried out in a volume of 0.1 mL in the presence of 1:M GDP-Fuc; (93,000 dpm), 10 mM $MnCl_2$, 20 mM Hepes pH 7.0, 0.05% Triton X-100 at 25° C. for 90 min. The reaction was halted by adding ethanol to a final concentration of 70%. Samples were incubated at 4° C. and filtered through 1.5:m glass fiber filters. The filters were washed with 70% ethanol containing 1 mM EDTA. The filters were dried and radioactivity determined by liquid scintillation. A control using pea Golgi vesicles was carried out in parallel. The results indicate that AtFT1 expressed in a COS cell line showed in vitro FTase activity that was 41 times higher than COS cells transformed with an empty vector and 1.4 times higher than solubilized pea Golgi vesicles.

Taken together, the in vitro translation data and the cos cell translation data provide strong evidence that AtFT1 is involved in xyloglucan biosynthesis.

Sequence Analysis of AtFT1

Analysis of AtFT1 indicates that, while it has some structural characteristics common to other fucosyltransferases, it is quite divergent at the amino acid sequence level. Hydrophobicity plots predict that there may be a N-terminal transmembrane signal anchor sequence. In vitro translation in the presence of canine pancreatic microsomes followed by carbonate washing of the products indicates that the AtFT1 translation product is a membrane protein (data not shown. As with other glycosyltransferases, the C-terminal region is predicted to be largely hydrophilic.

AtFT1 is not significantly similar to any other FTases from other organisms, although multiple sequence alignments have identified three motifs which appear to be conserved among all alpha 1,2-FTases. One ([IV]G[IV]HQ] [VI]R . . . [DN]; SEQ ID NO: 16) has been described previously (Breton et al., 1998). In addition, a second motif (D[EK] . . . F.[EQ].DQ; SEQ ID NO: 17) and a third hydrophobic region was conserved.

Since these proteins have different acceptor molecules but share the same sugar nucleotide donor (GDP-fucose), it is possible that these regions are involved in GDP-fucose binding or that are necessary for assumption of conserved structural characteristics. Some small regions of similarity are observed between AtFT1 and NodZ, a fucosyltransferase in Rhizobium involved in the synthesis of nodulation factors.

Other Glycosyltransferases

The unique nature of this FTase allow its use as a tool for identifying other glycosyltransferases. Consideration of the number of different linkages present in plant cell wall polysaccharides indicates that there should be several hundred different glycosyltransferases involved in cell wall biosynthesis. Several other sequences in the Arabidopsis databases do appear to be similar to AtFT1 and AtFT2 and thus might represent a multi-gene family of FTases or glycosyltransferases.

In addition to database analysis, the isolation of additional plant fucosyltransferases is made possible using standard molecular biology techniques. In particular, using all or a portion of the amino acid sequence of a plant fucosyltransferase of the invention, one may readily design fucosyltransferase oligonucleotide probes, including fucosyltransferase degenerate oligonucleotide probes (i.e., a mixture of all possible coding sequences for a given amino acid sequence). These oligonucleotides may be based upon the sequence of either strand of the DNA comprising the motif. General methods for designing and preparing such probes are provided, for example, in Ausubel et al., and Guide to Molecular Cloning Techniques, 1987, S. L. Berger and A. R. Kimmel, eds., Academic Press, New York. These oligonucleotides are useful for fucosyltransferase gene isolation, either through their use as probes capable of hybridizing to fucosyltransferase complementary sequences or as primers for various polymerase chain reaction (PCR) cloning strategies. In one particular example, isolation of other fucosyltransferase genes is performed by PCR amplification techniques well known to those skilled in the art of molecular biology using oligonucleotide primers designed to amplify only sequences flanked by the oligonucleotides in genes having sequence identity to fucosyltransferase of the invention. The primers are optionally designed to allow cloning of the amplified product into a suitable vector.

Hybridization techniques and procedures are well known to those skilled in the art and are described, for example, in Ausubel et al. If desired, a combination of different oligonucleotide probes may be used for the screening of the recombinant DNA library. The oligonucleotides are labelled with $^{32}$P using methods known in the art, and the detectably-labelled oligonucleotides are used to probe filter replicas from a recombinant DNA library. Recombinant DNA libraries may be prepared according to methods well known in the art, for example, as described in Ausubel et al., supra, or may be obtained from commercial sources.

For detection or isolation of closely related fucosyltransferases, high stringency conditions may be used; such conditions include hybridization at about 42 degrees C. and about 50% formamide; a first wash at about 65 degrees C., about 2×SSC, and 1% SDS; followed by a second wash at about 65 degrees C. and about 0.1% SDS, 1×SSC. Lower stringency conditions for detecting fucosyltransferase genes having about 85% sequence identity to the fucosyltransferase gene described herein include, for example, hybridization at about 42 degree C. in the absence of formamide; a first wash at about 42 degrees C., about 6×SSC, and about 1% SDS; and a second wash at about 50 degrees C., about 6×SSC, and about 1% SDS.

Fucosyltransferase oligonucleotides may also be used as primers in PCR cloning strategies. Such PCR methods are well known in the art and described, for example, in PCR Technology, H. A. Erlich, ed., Stockton Press, London, 1989; PCR Protocols: A Guide to Methods and Applications, M. A. Innis, D. H. Gelfand, J. J. Sninsky, and T. J. White, eds., Academic Press, Inc., New York, 1990; and Ausubel et al., supra. If desired, fucosyltransferases may be isolated using the PCR "RACE" technique, or Rapid Amplification of cDNA Ends (see, e.g., Innis et al., supra). By this method, oligonucleotide primers based on a fucosyltransferase conserved domain are oriented in the 3' and 5' directions and are used to generate overlapping PCR fragments. These overlapping 3'- and 5'-end RACE products are combined to produce an intact full-length cDNA. P.N.A.S. 85:8998 (1988)

Plant Transformation

Once identified, fucosyltransferase genes can be expressed in a variety of cells including plant cells, yeasts, fungi, bacterial cells and mammalian cells. A wide variety of plants can be transformed to express fucosyltransferase genes and genes related to fucosyltransferase in order to regulate plant carbohydrate glycosylation.

A. Dicots

Methods for transforming a wide variety of different dicots and obtaining transgenic plants are well documented in the literature (See Gasser and Fraley (1989) *Science* 244:1293; Fisk and Dandekar (1993) *Scientia Horticulturae* 55:5–36; Christou (1994) *Agro Food Industry Hi Tech* (March/April 1994) p.17, and the references cited therein).

B. Monocots

Methods for producing transgenic plants among the monocots are currently available. Successful transformation and plant regeneration have been achieved in asparagus (*Asparagus officinalis*; Bytebier et al. (1987) *Proc. Natl. Acad. Sci. USA* 84:5345); barley (*Hordeum vulgare*; Wan and Lemaux (1994) *Plant Physiol* 104:37); maize (*Zea mays*; Gordon-Kamm et al., (1990) *Plant Cell* 2:603; Fromm et al. (1990) *Bio/Technology* 8:833; Koziel et al. (1993) *Bio/Technology* 11:194); oats (*Avena sativa*, Somers et al. (1992) *Bio/Technology* 10:1589); orchardgrass (*Dactylis glomerata*; Horn et al. (1988) *Plant Cell Rep.* 7:469); rice (*Oryza sativa*, including indica and japonica varieties; Toriyama et al. (1988) *Bio/Technology* 6:10; Zhang et al. (1988) *Plant Cell Rep.* 7:379; Luo and Wu (1988) *Plant Mol. Biol. Rep.* 6:165; Zhang and Wu (1988) *Theor. Appl. Genet.* 76:835; Christou et al. (1991) *Bio/Technology* 9:957; rye (*Secale cereale*; De la Pena et al. (1987) *Nature* 325:274); sorghum (*Sorghum bicolor*, Cassas et al. (1993) *Proc. Natl. Acad. Sci. USA* 90:11212); sugar cane (Saccharum spp.; Bower and Birch (1992) *Plant J.* 2:409); tall fescue (*Festuca arundinacea*; Wang et al. (1992) *Bio/Technology* 10:691); turfgrass (*Agrostis palustris*; Zhong et al. (1993) *Plant Cell Rep.* 13:1); wheat (*Triticum aestivum*; Vasil et al. (1992) *Bio/Technology* 10:667; Troy Weeks et al. (1993) *Plant Physiol.* 102:1077; Becker et al. (1994) *Plant J.* 5:299).

C. Expression Vectors

A variety of expression vectors can be used to transfer the gene encoding plant fucosyltransferase activity as well as the desired promoters and regulatory proteins into a plant. Examples include but not limited to those derived from a Ti plasmid of *Agrobacterium tumefaciens*, as well as those disclosed by Herrera-Estrella, L., et al., Nature 303: 209 (1983), Bevan, M., Nucl. Acids Res. 12:8711–8721 (1984), Klee, H. J., Bio/Technology 3: 637–642 (1985), and EPO Publication 120,516 (Schilperoort et al.) for dicotyledonous plants. Alternatively, non-Ti vectors can be used to transfer the DNA constructs of this invention into monocotyledonous plants and plant cells by using free DNA delivery techniques. Such methods may involve, for example, the use of liposomes, electroporation, microprojectile bombardment, silicon carbide whiskers, viruses and pollen. By using these methods transgenic plants such as wheat, rice (Christou, P., Bio/Technology 9:957–962 (1991)) and corn (Gordon-Kamm, W., Plant Cell 2:603–618 (1990)) are produced. An immature embryo can also be a good target tissue for monocots for direct DNA delivery techniques by using the particle gun (Weeks, T. et al., Plant Physiol. 102:1077–1084 (1993); Vasil, V., Bio/Technology 10:667–674 (1993); Wan, Y. and Lemeaux, P., Plant Physiol. 104:37–48 (1994), and for Agrobacterium-mediated DNA transfer (Hiei et al., Plant J. 6:271–282 (1994); Rashid et al., Plant Cell Rep. 15:727–730 (1996); Dong, J., et al., Mol. Breeding 2:267–276 (1996); Aldemita, R. and Hodges, T., Planta 199:612–617 (1996); Ishida et al., Nature Biotech. 14:745–750 (1996)). In addition, plasmid pMEN020 is described in FIG. 1.

D. Plant Regeneration

After transformation of cells or protoplasts, the choice of methods for regenerating fertile plants is not particularly important. Suitable protocols are available for Leguminosae (alfalfa, soybean, clover, etc.), Umbelliferae (Carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops See protocols described in Ammirato et al. (1984) *Handbook of Plant Cell Culture—Crop Species*. Macmillan Publ. Co. Shimamoto et al. (1989) Nature 338:274–276; Fromm et al. (1990) *Bio/Technology* 8:833–839.; Vasil et al. (1990)Bio/Technology 8:429–434.

E. Carbohydrates from Transgenic Plants

Once transgenic plants are produced, carbohydrates can be isolated from the plants by procedures well known in the art. These purified carbohydrates are useful in agriculture as well medicine.

F. New Complex Carbohydrates

The enzymes involved in xyloglucan biosynthesis are reasonably stable and moderately abundant in plants. As such, these enzymes find use in synthesizing various types of complex carbohydrates under controlled conditions. It is also possible to make new complex carbohydrates that do not exist in Nature by procedures well known in the art.

G. Carbohydrates as Herbicides

Fucoxyloglucan (XG) is the major hemicellulosic polysaccharide in the primary cell wall of dicots. Monocots have small quantities of XG, but it seems to be much less important in all monocots including grasses. XG has a backbone of beta-1,4 linked glucosyl residues, with three out of every four residues substituted with xylose in a regular repeat, i.e. three substituted followed by one free. Approximately one out of six of the xylosyl residues is further substituted with galactose and on the two position of galactose is an alpha linked fucosyl residue. Thus, the fucose is a peripheral sugar in this polymer. However, the fucose has been postulated to be very important in determining the conformation of the polysaccharide, including controlling interactions of XG with cellulose. Thus, the presence of fucose may be important for the function of this polysaccharide.

Since XG is the major hemicellulosic polysaccharides in dicots, including many important weeds, but not very abundant in the cell walls of monocots, including corn, wheat, rice, barley, etc., inhibitors of XG synthesis may be valuable herbicides. Inhibitors include specific inhibitors of the enzyme itself and antisense constructs for inhibiting expression of the protein.

It appears that all of the enzymes that synthesize XG are part of a complex thereby permitting the use of XG-specific fucosyltransferase to identify other enzymes involved in XG synthesis. With the complete set of XG biosynthetic enzymes in hand, rationale herbicide design is feasible by procedures well known in the art.

We claim:

1. A method for producing a genetically transformed plant expressing fucosyltransferase wherein the method comprises:
   (a) transforming a plant cell with a vector encoding the plant fucosyltransferase as set forth in SEQ ID NO:1;
   (b) regenerating a plant from the plant cell; and
   (c) ensuring that the plant expresses the fucosyl transferase.

2. A transformed plant comprising a plant cell comprising a vector encoding the plant fucosyltransferase of SEQ ID NO:1, wherein the plant cell expresses the fucosyl transferase.

* * * * *

UNITED STATES PATENT AND TRADEMARK OFFICE
CERTIFICATE OF CORRECTION

PATENT NO. : 6,747,190 B1
DATED : June 8, 2004
INVENTOR(S) : Natasha V. Raikhel and Kenneth G. Keegstra It is certified that error appears in the above-identified patent and that said Letters Patent is hereby corrected as shown below:

Title page, Item [54] and Column 1, lines 1-3,
Title, "XYLOGLUCAN FUCOSYLTRANSFERASE PLANTS TRANSFORMED WITH A DNA ENCODING ARABIDOPSIS" should be -- PLANTS TRANSFORMED WITH A DNA ENCODING AN ARABIDOPSIS XYLOGLUCAN FUCOSYLTRANSFERASE --.

Column 4,
Line 44, "Substantially Pur Polypeptid:" should be -- Substantially Pure Polypeptide: --.

Column 6,
Lines 1 and 2, "was t centrifuged" should be -- was centrifuged --.

Column 7,
Line 6, "of XG with" should be -- of tXG with --.
Line 23, "rinsed in 505" should be -- rinsed in 50% --.
Line 64, "which is -60%" shoud be -- which is ~60% --.

Signed and Sealed this

Eighth Day of February, 2005

JON W. DUDAS
*Director of the United States Patent and Trademark Office*

SEQUENCE LISTING

```
<160> NUMBER OF SEQ ID NOS: 17

<210> SEQ ID NO 1
<211> LENGTH: 558
<212> TYPE: PRT
<213> ORGANISM: Arabidopsis thaliana

<400> SEQUENCE: 1

Met Asp Gln Asn Ser Tyr Arg Arg Arg Ser Ser Pro Ile Arg Thr Thr
1               5                   10                  15

Thr Gly Gly Ser Lys Ser Val Asn Phe Ser Glu Leu Leu Gln Met Lys
            20                  25                  30
```

-continued

```
Tyr Leu Ser Ser Gly Thr Met Lys Leu Thr Arg Thr Phe Thr Thr Cys
         35                  40                  45

Leu Ile Val Phe Ser Val Leu Val Ala Phe Ser Met Ile Phe His Gln
 50                  55                  60

His Pro Ser Asp Ser Asn Arg Ile Met Gly Phe Ala Glu Ala Arg Val
 65              70                  75                      80

Leu Asp Ala Gly Val Phe Pro Asn Val Thr Asn Ile Asn Ser Asp Lys
                 85                  90                  95

Leu Leu Gly Gly Leu Leu Ala Ser Gly Phe Asp Glu Asp Ser Cys Leu
            100                 105                 110

Ser Arg Tyr Gln Ser Val His Tyr Arg Lys Pro Ser Pro Tyr Lys Pro
            115                 120                 125

Ser Ser Tyr Leu Ile Ser Lys Leu Arg Asn Tyr Glu Lys Leu His Lys
            130                 135                 140

Arg Cys Gly Pro Gly Thr Glu Ser Tyr Lys Ala Leu Lys Gln Leu
145                 150                 155                 160

Asp Gln Glu His Ile Asp Gly Asp Gly Glu Cys Lys Tyr Val Val Trp
                165                 170                 175

Ile Ser Phe Ser Gly Leu Gly Asn Arg Ile Leu Ser Leu Ala Ser Val
                180                 185                 190

Phe Leu Tyr Ala Leu Leu Thr Asp Arg Val Leu Leu Val Asp Arg Gly
            195                 200                 205

Lys Asp Met Asp Asp Leu Phe Cys Glu Pro Phe Leu Gly Met Ser Trp
210                 215                 220

Leu Leu Pro Leu Asp Phe Pro Met Thr Asp Gln Phe Asp Gly Leu Asn
225                 230                 235                 240

Gln Glu Ser Ser Arg Cys Tyr Gly Tyr Met Val Lys Asn Gln Val Ile
                245                 250                 255

Asp Thr Glu Gly Thr Leu Ser His Leu Tyr Leu His Leu Val His Asp
                260                 265                 270

Tyr Gly Asp His Asp Lys Met Phe Phe Cys Glu Gly Asp Gln Thr Phe
            275                 280                 285

Ile Gly Lys Val Pro Trp Leu Ile Val Lys Thr Asp Asn Tyr Phe Val
290                 295                 300

Pro Ser Leu Trp Leu Ile Pro Gly Phe Asp Asp Glu Leu Asn Lys Leu
305                 310                 315                 320

Phe Pro Gln Lys Ala Thr Val Phe His His Leu Gly Arg Tyr Leu Phe
            325                 330                 335

His Pro Thr Asn Gln Val Trp Gly Leu Val Thr Arg Tyr Tyr Glu Ala
            340                 345                 350

Tyr Leu Ser His Ala Asp Glu Lys Ile Gly Ile Gln Val Arg Val Phe
            355                 360                 365

Asp Glu Asp Pro Gly Pro Phe Gln His Val Met Asp Gln Ile Ser Ser
            370                 375                 380

Cys Thr Gln Lys Glu Lys Leu Leu Pro Glu Val Asp Thr Leu Val Glu
385                 390                 395                 400

Arg Ser Arg His Val Asn Thr Pro Lys His Lys Ala Val Leu Val Thr
                405                 410                 415

Ser Leu Asn Ala Gly Tyr Ala Glu Asn Leu Lys Ser Met Tyr Trp Glu
            420                 425                 430

Tyr Pro Thr Ser Thr Gly Glu Ile Ile Gly Val His Gln Pro Ser Gln
            435                 440                 445
```

```
Glu Gly Tyr Gln Gln Thr Glu Lys Lys Met His Asn Gly Lys Ala Leu
    450                 455                 460
Ala Glu Met Tyr Leu Leu Ser Leu Thr Asp Asn Leu Val Thr Ser Ala
465                 470                 475                 480
Trp Ser Thr Phe Gly Tyr Val Ala Gln Gly Leu Gly Gly Leu Lys Pro
                485                 490                 495
Trp Ile Leu Tyr Arg Pro Glu Asn Arg Thr Thr Pro Asp Pro Ser Cys
            500                 505                 510
Gly Arg Ala Met Ser Met Glu Pro Cys Phe His Ser Pro Pro Phe Tyr
        515                 520                 525
Asp Cys Lys Ala Lys Thr Gly Ile Asp Thr Gly Thr Leu Val Pro His
    530                 535                 540
Val Arg His Cys Glu Asp Ile Ser Trp Gly Leu Lys Leu Val
545                 550                 555

<210> SEQ ID NO 2
<211> LENGTH: 1662
<212> TYPE: DNA
<213> ORGANISM: Arabidopsis thaliana

<400> SEQUENCE: 2
atggatcaga attcgtacag gagaagatcg tctccgatca gaaccactac cggcggttca      60
aagtccgtta atttctccga actacttcaa atgaagtatc tcagctccgg tacgatgaag     120
ctcacgagaa ccttcactac ttgcttgata gtcttctctg tactagtagc attctcaatg     180
atctttcacc aacacccatc tgattcaaat cggattatgg gtttcgccga agctagagtt     240
ctcgacgccg gagttttccc aaattctgat aagcttctcg gagggctact tgcttctggt     300
tttgatgaag attcttgcct tagtaggtac caatcagttc attaccgtaa accttcacct     360
tacaagccat cttcttatct catctctaag cttagaaaact acgaaaagct tcacaagcga     420
tgtggtccgg gtactgaatc ttacaagaaa gctctaaaac aacttgatca gaacatatt     480
gatggtgatg tgaatgcaa atatgttgtg tggatttctt ttagcggctt agggaacagg     540
atactttctc tagcctcggt ttttctttac gcgcttttaa cggatagagt cttgcttgtt     600
gaccgaggga agacatgga tgatctcttt tgcgagccgt ttctcggtat gtcgtggttg     660
ctacctttag atttccctat gactgatcag tttgatggat taaatcaaga atcatctcgt     720
tgttatggat atatggtgaa gaatcaggtg attgatactg agggaacttt gtctcatctt     780
tatcttcatc ttgttcatga ttatgagat catgataaga tgttcttctg tgaaggagac     840
caaacattca tcgggaaagt ccccttggttg attgttaaaa cagacaatta ctttgttcca     900
tctctgtggt taataccggg tttcgatgat gaactaaaca agctattccc acagaaagcg     960
actgtctttc atcacttagg taggtatctt tttcacccaa ctaaccaagt atggggctta    1020
gtcactagat actacgaagc ttacttatcg catgcggatg agaagattgg gattcaagta    1080
agagttttcg atgaagaccc gggtccattt cagcatgtga tggatcagat ttcatcttgt    1140
actcaaaaag agaaacttct acctgaagta gacacactag tggagagatc tcgccatgtt    1200
aataccccca acacaaagc cgtgcttgtc acatctttga acgcgggtta cgcggagaac    1260
ttaaagagta tgtattggga atatccgaca tcaactggaa aaatcatcgg tgttcatcag    1320
ccgagccaag aaggttatca gcagaccgaa aaaagatgc ataatggcaa agctcttgcg    1380
gaaatgtatc ttttgagttt gacagataat cttgtgacaa gtgcttggtc tacatttgga    1440
tatgtagctc aaggtcttgg aggtttaaag ccttggatac tctatagacc cgaaaaccgt    1500
```

-continued

| | |
|---|---|
| acaactcccg atccttcgtg tggtcgggct atgtcgatgg agccttgttt ccactcgcct | 1560 |
| ccattctatg attgtaaagc gaaaacgggt attgacacgg aacactagt tcctcatgtg | 1620 |
| agacattgtg aggatatcag ctggggactt aagctagtat ga | 1662 |

<210> SEQ ID NO 3
<211> LENGTH: 1953
<212> TYPE: DNA
<213> ORGANISM: Arabidopsis thaliana

<400> SEQUENCE: 3

| | |
|---|---|
| atggatcaga attcgtacag gagaagatcg tctccgatca gaaccactac cggcggttca | 60 |
| aagtccgtta atttctccga actacttcaa atgaagtatc tcagctccgg tacgatgaag | 120 |
| ctcacgagaa ccttcactac ttgcttgata gtcttctctg tactagtagc attctcaatg | 180 |
| atctttcacc aacacccatc tgattcaaat cggattatgg gtttcgccga agctagagtt | 240 |
| ctcgacgccg gagttttccc aaatgttact aacatcagta tgtgttcttc caagtcaaag | 300 |
| ttttgagctt tattacttta gatctcgttc tttacactac gcatttgcct ctgtatgtcc | 360 |
| atagctcttg gtcgatttca atttgagatc tatactcata aaaattgagt ctttgtcagt | 420 |
| cacaagacta ctatttttgg tttgatgttg ttttggtgaa aaagtgctct tttgttttgg | 480 |
| tctcagctta gactgttaca ttcgtttttt ccgagttttt tagattttgt tctgattctg | 540 |
| ttttgttttg tagattctga taagcttctc ggagggctac ttgcttctgg ttttgatgaa | 600 |
| gattcttgcc ttagtaggta ccaatcagtt cattaccgta accttcacc ttacaagcca | 660 |
| tcttcttatc tcatctctaa gcttagaaac tacgaaaagc ttcacaagcg atgtggtccg | 720 |
| ggtactgaat cttacaagaa agctctaaaa caacttgatc aagaacatat tgatggtgat | 780 |
| ggtgaatgca aatatgttgt gtggatttct tttagcggct tagggaacag gatactttct | 840 |
| ctagcctcgg ttttctttta cgcgctttta acggatagag tcttgcttgt tgaccgaggg | 900 |
| aaagacatgg atgatctctt ttgcgagccg tttctcggta tgtcgtggtt gctacctta | 960 |
| gatttcccta tgactgatca gtttgatgga ttaaatcaag aatcatctcg ttgttatgga | 1020 |
| tatatggtga agaatcaggt gattgatact gagggaactt tgtctcatct ttatcttcat | 1080 |
| cttgttcatg attatggaga tcatgataag atgttcttct gtgaaggaga ccaaacattc | 1140 |
| atcgggaaag tcccttggtt gattgttaaa acagacaatt actttgttcc atctctgtgg | 1200 |
| ttaataccgg gtttcgatga tgaactaaac aagctattcc cacagaaagc gactgtcttt | 1260 |
| catcacttag gtaggtatct ttttcaccca actaaccaag tatgggctt agtcactaga | 1320 |
| tactacgaag cttacttatc gcatgcggat gagaagattg ggattcaagt aagagttttc | 1380 |
| gatgaagacc cggtccatt tcagcatgtg atggatcaga tttcatcttg tactcaaaaa | 1440 |
| gagaaacttc tacctgaagt agacacacta gtggagagat ctcgccatgt taataccccc | 1500 |
| aaacacaaag ccgtgcttgt cacatctttg aacgcgggtt acgcggagaa cttaaagagt | 1560 |
| atgtattggg aatatccgac atcaactgga gaaatcatcg gtgttcatca gccgagccaa | 1620 |
| gaaggttatc agcagaccga aaaaagatg cataatggca aagctcttgc ggaaatgtat | 1680 |
| cttttgagtt tgacagataa tcttgtgaca agtgctggt ctacatttgg atatgtagct | 1740 |
| caaggtcttg gaggtttaaa gccttggata ctctatagac ccgaaaaccg tacaactccc | 1800 |
| gatccttcgt gtggtcgggc tatgtcgatg gagccttgtt tccactcgcc tccattctat | 1860 |
| gattgtaaag cgaaaacggg tattgacacg ggaacactag ttcctcatgt gagacattgt | 1920 |
| gaggatatca gctggggact taagctagta tga | 1953 |

<210> SEQ ID NO 4
<211> LENGTH: 1684
<212> TYPE: DNA
<213> ORGANISM: Arabidopsis thaliana

<400> SEQUENCE: 4

| | | | | | |
|---|---|---|---|---|---|
| atgagaatca | cagagatctt | agctttgttc | atggttttag | tccctgtctc | gctagtaatc | 60 |
| gtagccatgt | ttggatatga | tcaaggaaat | ggctttgtac | aagcatctag | attcataaca | 120 |
| atggaaccaa | atgtgacatc | ctcatcagat | gattcatcac | tagtgcagag | agatcaagaa | 180 |
| caaaaaggta | aacttacttt | cttcttttg | ttttgaaatg | tttctaaatt | tttctttgaa | 240 |
| tgtttcatca | gattctgtag | atatgtctct | gcttggaggg | ctacttgtat | ctggtttcaa | 300 |
| gaaagagtct | tgcttgagta | gataccaatc | ttacctctac | cgtaaagctt | caccgtataa | 360 |
| accttcgttg | catctacttt | cgaagcttag | agcttacgaa | gagcttcata | aagatgtgg | 420 |
| accgggaaca | agacagtata | ccaatgcaga | aagattgctt | aaacagaaac | aaacaggtga | 480 |
| gatggaatca | caaggatgca | agtatgttgt | ttggatgtcg | tttagcggat | aggaaacag | 540 |
| gattatcagt | attgcttctg | tgtttctgta | tgcaatgttg | acagatagag | tcttgcttgt | 600 |
| tgaaggaggg | gaacagttcg | cggatttatt | ctgcgaaccg | ttcctcgata | ccacttggtt | 660 |
| actaccgaaa | gatttcacct | tagctagtca | gttcagtggc | tttggtcaaa | actcagctca | 720 |
| ctgccatgga | gatatgctga | gaggaaaact | gattaatgaa | tcctctgttt | cgtctctgtc | 780 |
| tcatctctat | cttcatctag | ctcatgacta | caatgagcac | gacaaaatgt | tcttctgtga | 840 |
| agaagatcaa | aatctcttaa | agaatgttcc | ttggttgatc | atgaggacaa | acaacttctt | 900 |
| tgcaccgtct | ctttcttga | tttcttcttt | cgaagaagag | ctcggtatga | tgtttcccga | 960 |
| gaaaggaacg | gttttccacc | atttaggtcg | ttaccttttc | catccttcaa | atcaagtctg | 1020 |
| gggactaatc | acaagatact | atcaagctta | cttagccaaa | gctgatgaaa | ggattggtct | 1080 |
| tcaaataaga | gtctttgatg | agaaatccgg | cgtatctcct | cgagtcacaa | agcaaatcat | 1140 |
| ttcgtgtgtt | caaaacgaga | atctgttacc | gagactaagc | aaaggtgaag | aacaatacaa | 1200 |
| gcagccatca | gaagaagagt | tgaaactcaa | atctgtcttg | gtcacctctt | taacaacagg | 1260 |
| atactttgag | atcttgaaaa | caatgtattg | ggaaaatcca | actgtaacaa | gagatgtgat | 1320 |
| tggaatacat | cagccaagtc | atgaaggaca | tcaacaaaca | gagaagctaa | tgcataacag | 1380 |
| gaaagcttgg | gcagagatgt | acttactcag | cttaacggat | aagttggtta | ttagtgcttg | 1440 |
| gtctacattt | ggttatgtag | ctcaaggact | tggaggatta | agagcttgga | ttctgtataa | 1500 |
| acaagagaat | caaaccaacc | caaatccacc | ttgcggtaga | gctatgtcac | cagatccttg | 1560 |
| tttccatgct | cctccttact | atgattgcaa | agcaaagaaa | ggaactgaca | ctggtaatgt | 1620 |
| tgtcccgcat | gttagacatt | gtgaagatat | tagctgggga | cttaagcttg | ttgacaactt | 1680 |
| ttag | | | | | | 1684 |

<210> SEQ ID NO 5
<211> LENGTH: 538
<212> TYPE: PRT
<213> ORGANISM: Arabidopsis thaliana

<400> SEQUENCE: 5

Met Arg Ile Thr Glu Ile Leu Ala Leu Phe Met Val Leu Val Pro Val
1               5                   10                  15

Ser Leu Val Ile Val Ala Met Phe Gly Tyr Asp Gln Gly Asn Gly Phe

```
                    20                  25                  30
Val Gln Ala Ser Arg Phe Ile Thr Met Glu Pro Asn Val Thr Ser Ser
             35                  40                  45
Ser Asp Asp Ser Ser Leu Val Gln Arg Asp Gln Glu Gln Lys Asp Ser
     50                  55                  60
Val Asp Met Ser Leu Leu Gly Leu Leu Val Ser Gly Phe Lys Lys
 65                  70                  75                  80
Glu Ser Cys Leu Ser Arg Tyr Gln Ser Tyr Leu Tyr Arg Lys Ala Ser
                 85                  90                  95
Pro Tyr Lys Pro Ser Leu Leu Ser Lys Leu Arg Ala Tyr Glu Glu
             100                 105                 110
Leu His Lys Arg Cys Gly Pro Gly Thr Arg Gln Tyr Thr Asn Ala Glu
             115                 120                 125
Arg Leu Leu Lys Gln Lys Gln Thr Gly Glu Met Glu Ser Gln Gly Cys
         130                 135                 140
Lys Tyr Val Val Trp Met Ser Phe Ser Gly Leu Gly Asn Arg Ile Ile
145                 150                 155                 160
Ser Ile Ala Ser Val Phe Leu Tyr Ala Met Leu Thr Asp Arg Val Leu
                 165                 170                 175
Leu Val Glu Gly Gly Glu Gln Phe Ala Asp Leu Phe Cys Glu Pro Phe
             180                 185                 190
Leu Asp Thr Thr Trp Leu Leu Pro Lys Asp Phe Thr Leu Ala Ser Gln
             195                 200                 205
Phe Ser Gly Phe Gly Gln Asn Ser Ala His Cys His Gly Asp Met Leu
         210                 215                 220
Lys Arg Lys Leu Ile Asn Glu Ser Ser Val Ser Ser Leu Ser His Leu
225                 230                 235                 240
Tyr Leu His Leu Ala His Asp Tyr Asn Glu His Asp Lys Met Phe Phe
                 245                 250                 255
Cys Glu Glu Asp Gln Asn Leu Leu Lys Asn Val Pro Trp Leu Ile Met
             260                 265                 270
Arg Thr Asn Asn Phe Phe Ala Pro Ser Leu Phe Leu Ile Ser Ser Phe
         275                 280                 285
Glu Glu Glu Leu Gly Met Met Phe Pro Glu Lys Gly Thr Val Phe His
     290                 295                 300
His Leu Gly Arg Tyr Leu Phe His Pro Ser Asn Gln Val Trp Gly Leu
305                 310                 315                 320
Ile Thr Arg Tyr Tyr Gln Ala Tyr Leu Ala Lys Ala Asp Glu Arg Ile
                 325                 330                 335
Gly Leu Gln Ile Arg Val Phe Asp Glu Lys Ser Gly Val Ser Pro Arg
             340                 345                 350
Val Thr Lys Gln Ile Ile Ser Cys Val Gln Asn Glu Asn Leu Leu Pro
         355                 360                 365
Arg Leu Ser Lys Gly Glu Gln Tyr Lys Gln Pro Ser Glu Glu Glu
     370                 375                 380
Leu Lys Leu Lys Ser Val Leu Val Thr Ser Leu Thr Thr Gly Tyr Phe
385                 390                 395                 400
Glu Ile Leu Lys Thr Met Tyr Trp Glu Asn Pro Thr Val Thr Arg Asp
                 405                 410                 415
Val Ile Gly Ile His Gln Pro Ser His Glu Gly His Gln Gln Thr Glu
             420                 425                 430
Lys Leu Met His Asn Arg Lys Ala Trp Ala Glu Met Tyr Leu Leu Ser
         435                 440                 445
```

```
Leu Thr Asp Lys Leu Val Ile Ser Ala Trp Ser Thr Phe Gly Tyr Val
    450                 455                 460

Ala Gln Gly Leu Gly Gly Leu Arg Ala Trp Ile Leu Tyr Lys Gln Glu
465                 470                 475                 480

Asn Gln Thr Asn Pro Asn Pro Pro Cys Gly Arg Ala Met Ser Pro Asp
                485                 490                 495

Pro Cys Phe His Ala Pro Pro Tyr Tyr Asp Cys Lys Ala Lys Lys Gly
                500                 505                 510

Thr Asp Thr Gly Asn Val Val Pro His Val Arg His Cys Glu Asp Ile
        515                 520                 525

Ser Trp Gly Leu Lys Leu Val Asp Asn Phe
    530                 535
```

<210> SEQ ID NO 6
<211> LENGTH: 252
<212> TYPE: DNA
<213> ORGANISM: Arabidopsis thaliana
<220> FEATURE:
<221> NAME/KEY: misc_feature
<222> LOCATION: (10)..(10)
<223> OTHER INFORMATION: "n" is A, C, G, or T
<220> FEATURE:
<221> NAME/KEY: misc_feature
<222> LOCATION: (101)..(101)
<223> OTHER INFORMATION: "n" is A, C, G, or T
<220> FEATURE:
<221> NAME/KEY: misc_feature
<222> LOCATION: (133)..(133)
<223> OTHER INFORMATION: "n" is A, C, G, or T
<220> FEATURE:
<221> NAME/KEY: misc_feature
<222> LOCATION: (147)..(147)
<223> OTHER INFORMATION: "n" is A, C, G, or T
<220> FEATURE:
<221> NAME/KEY: misc_feature
<222> LOCATION: (168)..(168)
<223> OTHER INFORMATION: "n" is A, C, G, or T
<220> FEATURE:
<221> NAME/KEY: misc_feature
<222> LOCATION: (197)..(197)
<223> OTHER INFORMATION: "n" is A, C, G, or T
<220> FEATURE:
<221> NAME/KEY: misc_feature
<222> LOCATION: (215)..(215)
<223> OTHER INFORMATION: "n" is A, C, G, or T
<220> FEATURE:
<221> NAME/KEY: misc_feature
<222> LOCATION: (29)..(29)
<223> OTHER INFORMATION: "n" is A, C, G, or T
<220> FEATURE:
<221> NAME/KEY: misc_feature
<222> LOCATION: (61)..(61)
<223> OTHER INFORMATION: "n" is A, C, G, or T
<220> FEATURE:
<221> NAME/KEY: misc_feature
<222> LOCATION: (92)..(92)
<223> OTHER INFORMATION: "n" is A, C, G, or T

<400> SEQUENCE: 6
tgttccatcn ttatggttta atccaactnt ccaaaccgaa ctaacgaagc tgtttccgca      60
naaagaaacc gtgtttcacc acttgggtcg gnatctttttt naccctaaaa atcaagtttg    120
ggatatcgtc acnaagtact accatgntca cttatccaaa gcagatgnga gactcgggat    180
tcaaattcgg gttttttngcg atcaaggtgg atacnaccaa cacgtcatgg accaggtcat    240
atcctgcaca ca                                                         252

<210> SEQ ID NO 7

```
<211> LENGTH: 83
<212> TYPE: PRT
<213> ORGANISM: Arabidopsis thaliana
<220> FEATURE:
<221> NAME/KEY: misc_feature
<222> LOCATION: (10)..(10)
<223> OTHER INFORMATION: "X" is any amino acid
<220> FEATURE:
<221> NAME/KEY: misc_feature
<222> LOCATION: (20)..(20)
<223> OTHER INFORMATION: "X" is any amino acid
<220> FEATURE:
<221> NAME/KEY: misc_feature
<222> LOCATION: (31)..(31)
<223> OTHER INFORMATION: "X" is any amino acid
<220> FEATURE:
<221> NAME/KEY: misc_feature
<222> LOCATION: (34)..(34)
<223> OTHER INFORMATION: "X" is any amino acid
<220> FEATURE:
<221> NAME/KEY: misc_feature
<222> LOCATION: (49)..(49)
<223> OTHER INFORMATION: "X" is any amino acid
<220> FEATURE:
<221> NAME/KEY: misc_feature
<222> LOCATION: (56)..(56)
<223> OTHER INFORMATION: "X" is any amino acid
<220> FEATURE:
<221> NAME/KEY: misc_feature
<222> LOCATION: (66)..(66)
<223> OTHER INFORMATION: "X" is any amino acid
<220> FEATURE:
<221> NAME/KEY: misc_feature
<222> LOCATION: (72)..(72)
<223> OTHER INFORMATION: "X" is any amino acid

<400> SEQUENCE: 7

Val Pro Ser Leu Trp Phe Asn Pro Thr Xaa Gln Thr Glu Leu Thr Lys
 1               5                  10                  15

Leu Phe Pro Xaa Lys Glu Thr Val Phe His His Leu Gly Arg Xaa Leu
            20                  25                  30

Phe Xaa Pro Lys Asn Gln Val Trp Asp Ile Val Thr Lys Tyr Tyr His
        35                  40                  45

Xaa His Leu Ser Lys Ala Asp Xaa Arg Leu Gly Ile Gln Ile Arg Val
    50                  55                  60

Phe Xaa Asp Gln Gly Gly Tyr Xaa Gln His Val Met Asp Gln Val Ile
65                  70                  75                  80

Ser Cys Thr

<210> SEQ ID NO 8
<211> LENGTH: 512
<212> TYPE: DNA
<213> ORGANISM: Arabidopsis thaliana
<220> FEATURE:
<221> NAME/KEY: misc_feature
<222> LOCATION: (146)..(146)
<223> OTHER INFORMATION: "n" is A, C, G, or T
<220> FEATURE:
<221> NAME/KEY: misc_feature
<222> LOCATION: (190)..(190)
<223> OTHER INFORMATION: "n" is A, C, G, or T
<220> FEATURE:
<221> NAME/KEY: misc_feature
<222> LOCATION: (195)..(195)
<223> OTHER INFORMATION: "n" is A, C, G, or T
<220> FEATURE:
<221> NAME/KEY: misc_feature
<222> LOCATION: (224)..(224)
<223> OTHER INFORMATION: "n" is A, C, G, or T
<220> FEATURE:
<221> NAME/KEY: misc_feature
<222> LOCATION: (263)..(263)
```

```
<223> OTHER INFORMATION: "n" is A, C, G, or T
<220> FEATURE:
<221> NAME/KEY: misc_feature
<222> LOCATION: (29)..(29)
<223> OTHER INFORMATION: "n" is A, C, G, or T
<220> FEATURE:
<221> NAME/KEY: misc_feature
<222> LOCATION: (354)..(354)
<223> OTHER INFORMATION: "n" is A, C, G, or T
<220> FEATURE:
<221> NAME/KEY: misc_feature
<222> LOCATION: (382)..(383)
<223> OTHER INFORMATION: "n" is A, C, G, or T
<220> FEATURE:
<221> NAME/KEY: misc_feature
<222> LOCATION: (397)..(397)
<223> OTHER INFORMATION: "n" is A, C, G, or T
<220> FEATURE:
<221> NAME/KEY: misc_feature
<222> LOCATION: (4)..(4)
<223> OTHER INFORMATION: "n" is A, C, G, or T
<220> FEATURE:
<221> NAME/KEY: misc_feature
<222> LOCATION: (408)..(408)
<223> OTHER INFORMATION: "n" is A, C, G, or T
<220> FEATURE:
<221> NAME/KEY: misc_feature
<222> LOCATION: (426)..(426)
<223> OTHER INFORMATION: "n" is A, C, G, or T
<220> FEATURE:
<221> NAME/KEY: misc_feature
<222> LOCATION: (433)..(434)
<223> OTHER INFORMATION: "n" is A, C, G, or T
<220> FEATURE:
<221> NAME/KEY: misc_feature
<222> LOCATION: (438)..(438)
<223> OTHER INFORMATION: "n" is A, C, G, or T
<220> FEATURE:
<221> NAME/KEY: misc_feature
<222> LOCATION: (454)..(454)
<223> OTHER INFORMATION: "n" is A, C, G, or T
<220> FEATURE:
<221> NAME/KEY: misc_feature
<222> LOCATION: (481)..(481)
<223> OTHER INFORMATION: "n" is A, C, G, or T
<220> FEATURE:
<221> NAME/KEY: misc_feature
<222> LOCATION: (489)..(489)
<223> OTHER INFORMATION: "n" is A, C, G, or T
<220> FEATURE:
<221> NAME/KEY: misc_feature
<222> LOCATION: (511)..(511)
<223> OTHER INFORMATION: "n" is A, C, G, or T

<400> SEQUENCE: 8
tggnattaca gattacaaag atacgaggnt cttcatagac gttgtggacc attcactaga      60
tcctataact taaacacttga caaactcaag tcgggagatc ggtctgacgg tgaagtttct    120
ggttgtagat atgtaatatg gttganttcc aatggtgatc ttgggaatag gatgctgagt    180
ctagcttcan ctttnctttn atgctctctta acaaataggt tttnacttgt cgaactagga    240
gttgacatgg ctgatctttt ctncgagcca tttccaaaca ctacttggtt tcttccccca    300
gagtttccgc tcaacagcca cttcaacgag caagtctctt tctaacgaa attnttggca     360 accccgatgg gttcataatc gnncatgtag ttccgtnatt cccagtgncc aacaaaaagc    420
tttttntttt tgnnaggnta gccaagtttt tttngggaa accccctggt tgtcttaaaa     480
ncgggtagnt ttttttttccc aactttttttt na                                512

<210> SEQ ID NO 9
<211> LENGTH: 668
<212> TYPE: DNA
<213> ORGANISM: Arabidopsis thaliana
```

<400> SEQUENCE: 9

```
caagcttaca agaaagcaac ggagattctt ggtcatgatg atgagaatca ttcaaccaaa    60
tctgttggtg aatgcagata cattgtgtgg attgctgttt atgggctagg aaacagaata   120
cttactcttg cttctctgtt tctctatgct ctcttgactg acagaatcat gcttgttgac   180
caacgtacgg acataagtga cctcttcgt gagccttttc caggtacttc ctggctactc   240
cctctggatt ttccactaac agatcaatta gatagcttca acaaggaatc tccgcgctgt   300
tacgaacaa tgttgaagaa tcatgccatt aactcaacta caacagaaag catcatcccc   360
tcgtacctct gtctttatct tattcacgat tacgacgatt atgataagat gttcttctgt   420
gaaagtgacc aaattctcat caggcaagtc ccttggttgg tcttcaactc gaatctttac   480
tttatcccat ctctatggtt gatcccttct tttcagtcag aattaagcaa gctattccca   540
cagaaagaaa ccgtctttca ccatttggct cgctatcttt ttcacccgac taaccaagtt   600
tggggcatga tcacaagatc ctataatggg tatttatcaa gagctgatga gagacttggg   660
attcaagt                                                            668
```

<210> SEQ ID NO 10
<211> LENGTH: 671
<212> TYPE: DNA
<213> ORGANISM: Arabidopsis thaliana

<400> SEQUENCE: 10

```
ttctccttt gacctttttt tttgttatat gttcagacga atccgaaaca ccggggcggg    60
atagactaat aggagggctt ttaaccgcag atttcgatga aggttcttgc ttgagtaggt   120
atcataaaac tttcttgtat cgcaagcctt caccatacaa gccgtctgaa tatcttgtct   180
cgaagcttag aagctatgag atgcttcaca acgttgcgg tccagggaca aaagcttaca   240
aggaagcaac aaagcatctt agtcatgatg agaattataa tgcaagcaaa tcagatggtg   300
aatgccgata cgttgtgtgg ctcgctgatt acgggcttgg aaaccgacta ctcactcttg   360
cttctgtgtt cctctacgct ctcttgactg atagaatcat tcttgttgac aaccgcaagg   420
atattggtga tctcttatgc gagccatttc aggtacttc atggttgctt cctctcgact   480
ttccattgat gaaatatgct gatggatacc acaagggata ctctcgttgt tacggaacaa   540
tgttggaaaa tcattccatc aactcgactt cattcccgcc acatctatat aggcataacc   600
ttcatgattc aagggatagt gataagatgt tcttctgcca aaaagatcaa agtttgattg   660
acaaagtccc t                                                        671
```

<210> SEQ ID NO 11
<211> LENGTH: 785
<212> TYPE: DNA
<213> ORGANISM: Arabidopsis thaliana
<220> FEATURE:
<221> NAME/KEY: misc_feature
<222> LOCATION: (148)..(148)
<223> OTHER INFORMATION: "n" is A, C, G, or T
<220> FEATURE:
<221> NAME/KEY: misc_feature
<222> LOCATION: (150)..(150)
<223> OTHER INFORMATION: "n" is A, C, G, or T
<220> FEATURE:
<221> NAME/KEY: misc_feature
<222> LOCATION: (221)..(221)
<223> OTHER INFORMATION: "n" is A, C, G, or T
<220> FEATURE:
<221> NAME/KEY: misc_feature
<222> LOCATION: (248)..(248)

<223> OTHER INFORMATION: "n" is A, C, G, or T
<220> FEATURE:
<221> NAME/KEY: misc_feature
<222> LOCATION: (330)..(330)
<223> OTHER INFORMATION: "n" is A, C, G, or T
<220> FEATURE:
<221> NAME/KEY: misc_feature
<222> LOCATION: (382)..(382)
<223> OTHER INFORMATION: "n" is A, C, G, or T
<220> FEATURE:
<221> NAME/KEY: misc_feature
<222> LOCATION: (410)..(410)
<223> OTHER INFORMATION: "n" is A, C, G, or T
<220> FEATURE:
<221> NAME/KEY: misc_feature
<222> LOCATION: (422)..(422)
<223> OTHER INFORMATION: "n" is A, C, G, or T
<220> FEATURE:
<221> NAME/KEY: misc_feature
<222> LOCATION: (451)..(451)
<223> OTHER INFORMATION: "n" is A, C, G, or T
<220> FEATURE:
<221> NAME/KEY: misc_feature
<222> LOCATION: (502)..(502)
<223> OTHER INFORMATION: "n" is A, C, G, or T
<220> FEATURE:
<221> NAME/KEY: misc_feature
<222> LOCATION: (509)..(509)
<223> OTHER INFORMATION: "n" is A, C, G, or T
<220> FEATURE:
<221> NAME/KEY: misc_feature
<222> LOCATION: (528)..(528)
<223> OTHER INFORMATION: "n" is A, C, G, or T
<220> FEATURE:
<221> NAME/KEY: misc_feature
<222> LOCATION: (539)..(539)
<223> OTHER INFORMATION: "n" is A, C, G, or T
<220> FEATURE:
<221> NAME/KEY: misc_feature
<222> LOCATION: (549)..(549)
<223> OTHER INFORMATION: "n" is A, C, G, or T
<220> FEATURE:
<221> NAME/KEY: misc_feature
<222> LOCATION: (647)..(647)
<223> OTHER INFORMATION: "n" is A, C, G, or T
<220> FEATURE:
<221> NAME/KEY: misc_feature
<222> LOCATION: (650)..(650)
<223> OTHER INFORMATION: "n" is A, C, G, or T
<220> FEATURE:
<221> NAME/KEY: misc_feature
<222> LOCATION: (659)..(659)
<223> OTHER INFORMATION: "n" is A, C, G, or T
<220> FEATURE:
<221> NAME/KEY: misc_feature
<222> LOCATION: (701)..(702)
<223> OTHER INFORMATION: "n" is A, C, G, or T

<400> SEQUENCE: 11

```
gggggggatg gttactgact cctatatgcc gaatctttga catctctgtt tcaatggcca      60
caatcctatt gaatcagcta tattaaagaa aattataact catcaaatag cttaagacca     120
tcgttcccac gatcctcaca atgccttncn agaggaacta ccttcccgga gttagttccc     180
cattcgggtt cacatccatg agacggaaga gtaaggtgac natggtccat cgacgtggat     240
tgaatacnct gtggatcagg agctgtacga cctgctggct gataaagtaa ccatggcttt     300
aatcctccaa gaatatgagc aacatatccn aatgtagacc ttgcacttgt gactatttta     360
tcagttagac ttagaagata cntctcggcg agcgcctttt ggtcgtgtan cttcttgtct     420
tntgttgaac cctttctcca cttggctgat naacttcaat gatctcccct gctgaactcg     480
gtcgttccca atacatgttc tntaaggtnt cagagtactc tggatacnaa gatgtgacna     540
gaacagctnt aagtgtctgg cttcttgaat atatgacttt tggctcttct tgtgcacctt     600
```

```
gttcaggcaa aaggtctctc ttcctgtcca acttacaact tgatccnttn cctgttaana    660
tttccccctc gaatgctgaa ctacccttc tctaataacc nncctctcct ccgctcctga    720
ataacttcgg cttgctagaa ttctctcatt cacctcccca cttgaccccc ccgcggtac    780 aaacc                                                                785
```

```
<210> SEQ ID NO 12
<211> LENGTH: 529
<212> TYPE: DNA
<213> ORGANISM: Arabidopsis thaliana
<220> FEATURE:
<221> NAME/KEY: misc_feature
<222> LOCATION: (276)..(276)
<223> OTHER INFORMATION: "n" is A, C, G, or T
<220> FEATURE:
<221> NAME/KEY: misc_feature
<222> LOCATION: (361)..(361)
<223> OTHER INFORMATION: "n" is A, C, G, or T
<220> FEATURE:
<221> NAME/KEY: misc_feature
<222> LOCATION: (386)..(386)
<223> OTHER INFORMATION: "n" is A, C, G, or T
<220> FEATURE:
<221> NAME/KEY: misc_feature
<222> LOCATION: (409)..(409)
<223> OTHER INFORMATION: "n" is A, C, G, or T
<220> FEATURE:
<221> NAME/KEY: misc_feature
<222> LOCATION: (433)..(433)
<223> OTHER INFORMATION: "n" is A, C, G, or T
<220> FEATURE:
<221> NAME/KEY: misc_feature
<222> LOCATION: (481)..(481)
<223> OTHER INFORMATION: "n" is A, C, G, or T
<220> FEATURE:
<221> NAME/KEY: misc_feature
<222> LOCATION: (490)..(490)
<223> OTHER INFORMATION: "n" is A, C, G, or T

<400> SEQUENCE: 12
attcgtgatg agtactatgc aagcgaatca aatggtgact gcagatacat tgtatggcta     60
gctagggacg ggcttggaaa cagattaatt actcttgctt ccgtgtttct ctacgctatc    120
ttgactgaga gaatcattct tgttgacaac cgcaaggatg ttagtgatct cttatgtgag    180
ccatttccag gtacttcatg gttgcttccg cttgactttc caatgctgaa ttatacttat    240
gcttatggct acaataagga atacctcgtt gttacngtac aatgttggaa aatcatgcca    300
tcaactcgac ttcaattccg ccacatctat atctccataa catccatgaa tctagggata    360
ntgataagct gttcttctgc caaaanggat caaagttttt tatcgacana tttccatggg    420
taaattaatt canaaccaat gccttacttt ggttcccaat ctttatgggc tgaaatccca    480
ncttttccan accaaaaact aagtttaagc ttatccccgg cagaaaagg              529
```

```
<210> SEQ ID NO 13
<211> LENGTH: 290
<212> TYPE: DNA
<213> ORGANISM: Arabidopsis thaliana

<400> SEQUENCE: 13
aatggtgatc ttgggaatag gatgctgagt ctagcttcag cttttcttta tgctctctta     60
acaaataggt ttaacttgt cgaactagga gttgacatgg ctgaccttt ctgcaagcca    120 tttccaaaca ctacttggtt tctcccccca gagtttccgc tcaacagcca cttcaacgag    180
cagtctcttc tacgcaattc tggcaacccg atggttgcat atcgacatgt agttcgtgaa    240
```
ttccagtgac caacaaaagc ttttcttttg tgaggatagt caagttttgt         290

<210> SEQ ID NO 14
<211> LENGTH: 207
<212> TYPE: DNA
<213> ORGANISM: Arabidopsis thaliana

<400> SEQUENCE: 14
caagcttcga gacaagatat tcagacggct tgtatggtga aggcttgcga tacaagaaag   60
ttttatgata cctactcaag caagaacctt catcgaaatc tgcggttaaa agccctccta  120
ttagtctatc ccgccccggt gtttcggatt cgtctgaaca tataacaaaa aaaaaggtca  180
aaaggagaat tctttgagct aacaatg                                     207

<210> SEQ ID NO 15
<211> LENGTH: 531
<212> TYPE: DNA
<213> ORGANISM: Arabidopsis thaliana
<220> FEATURE:
<221> NAME/KEY: misc_feature
<222> LOCATION: (12)..(12)
<223> OTHER INFORMATION: "n" is A, C, G, or T
<220> FEATURE:
<221> NAME/KEY: misc_feature
<222> LOCATION: (147)..(147)
<223> OTHER INFORMATION: "n" is A, C, G, or T
<220> FEATURE:
<221> NAME/KEY: misc_feature
<222> LOCATION: (153)..(153)
<223> OTHER INFORMATION: "n" is A, C, G, or T
<220> FEATURE:
<221> NAME/KEY: misc_feature
<222> LOCATION: (159)..(159)
<223> OTHER INFORMATION: "n" is A, C, G, or T
<220> FEATURE:
<221> NAME/KEY: misc_feature
<222> LOCATION: (16)..(16)
<223> OTHER INFORMATION: "n" is A, C, G, or T
<220> FEATURE:
<221> NAME/KEY: misc_feature
<222> LOCATION: (168)..(168)
<223> OTHER INFORMATION: "n" is A, C, G, or T
<220> FEATURE:
<221> NAME/KEY: misc_feature
<222> LOCATION: (205)..(205)
<223> OTHER INFORMATION: "n" is A, C, G, or T
<220> FEATURE:
<221> NAME/KEY: misc_feature
<222> LOCATION: (27)..(27)
<223> OTHER INFORMATION: "n" is A, C, G, or T
<220> FEATURE:
<221> NAME/KEY: misc_feature
<222> LOCATION: (275)..(275)
<223> OTHER INFORMATION: "n" is A, C, G, or T
<220> FEATURE:
<221> NAME/KEY: misc_feature
<222> LOCATION: (4)..(5)
<223> OTHER INFORMATION: "n" is A, C, G, or T
<220> FEATURE:
<221> NAME/KEY: misc_feature
<222> LOCATION: (50)..(50)
<223> OTHER INFORMATION: "n" is A, C, G, or T
<220> FEATURE:
<221> NAME/KEY: misc_feature
<222> LOCATION: (53)..(53)
<223> OTHER INFORMATION: "n" is A, C, G, or T
<220> FEATURE:
<221> NAME/KEY: misc_feature
<222> LOCATION: (72)..(73)
<223> OTHER INFORMATION: "n" is A, C, G, or T
<220> FEATURE:
<221> NAME/KEY: misc_feature
<222> LOCATION: (81)..(81)
<223> OTHER INFORMATION: "n" is A, C, G, or T

```
<220> FEATURE:
<221> NAME/KEY: misc_feature
<222> LOCATION: (87)..(87)
<223> OTHER INFORMATION: "n" is A, C, G, or T
<220> FEATURE:
<221> NAME/KEY: misc_feature
<222> LOCATION: (98)..(98)
<223> OTHER INFORMATION: "n" is A, C, G, or T
<220> FEATURE:
<221> NAME/KEY: misc_feature
<222> LOCATION: (118)..(118)
<223> OTHER INFORMATION: "n" is A, C, G, or T

<400> SEQUENCE: 15
aaanncctta ancaantttt accgaantca aggcgtttac ccacttctcn ccnggtttta      60
aggttcaggg cnnttttttgg naacccnaca gtgatggnga gttatccgcg ttcacaancc    120
gactacaagg cttccaaaaa cccccgngga acntggaant taagaganca tggctgagat    180
ataccttctg agttgttctg atgcnctggt ggtcacaggt ttatggtcct cactcgtgga    240
ggttgcctca tggccttgga gggttgaagc catgngtgtt gaacaaagct gagaatggga    300
ctgcccatga gccttactgt gtgaaagcaa gatcaataga gccctgttcc caagcgacat    360
tgttccatgg ctgtaaagat tgaaacatga atagagtctc gagggctttt tttgccttta    420
atagatgttg tacggtcaag aatttcagag ttgcccaata gacacgtaag gaatattagg    480
attaactatg tatcagttca tgacttgatc gagttctata ttcttttcaa t             531

<210> SEQ ID NO 16
<211> LENGTH: 12
<212> TYPE: PRT
<213> ORGANISM: Cross-species

<400> SEQUENCE: 16

Ile Val Gly Ile Val His Gln Val Ile Arg Asp Asn
1               5                   10

<210> SEQ ID NO 17
<211> LENGTH: 8
<212> TYPE: PRT
<213> ORGANISM: Cross-species

<400> SEQUENCE: 17

Asp Glu Lys Phe Glu Gln Asp Gln
1               5
```